United States Patent [19]

Riess

[11] Patent Number: 4,891,123
[45] Date of Patent: Jan. 2, 1990

[54] ELECTROCHEMICAL ANALYZER FOR MEASURING THE CONCENTRATION OF ATOMS OR MOLECULES IN A FLUID AND METHOD OF MAKING SAME

[75] Inventor: Ilan Riess, Moshav Beit Shearim, Israel

[73] Assignee: Frantztech Ltd., New York, N.Y.

[21] Appl. No.: 179,584

[22] Filed: Apr. 8, 1988

[30] Foreign Application Priority Data

Apr. 10, 1987 [IL] Israel ......................... 82160

[51] Int. Cl.⁴ ............................................. G01N 27/46
[52] U.S. Cl. .................................. 204/427; 204/424; 264/104; 264/109
[58] Field of Search ........ 204/1 S, 421, 424, 427–429; 264/104, 109

[56] References Cited

U.S. PATENT DOCUMENTS

| | | | |
|---|---|---|---|
| 3,400,054 | 9/1968 | Ruka et al. | 204/427 |
| 3,503,809 | 3/1970 | Spacil | 204/427 |
| 3,598,711 | 8/1971 | Flais | 204/427 |
| 3,616,408 | 10/1971 | Hickam | 204/427 |
| 3,620,931 | 11/1971 | Reichner | 204/427 |
| 3,691,023 | 9/1972 | Ruka et al. | 204/425 |
| 3,768,259 | 10/1973 | Carnahan et al. | 204/426 |
| 3,791,937 | 2/1974 | Besson et al. | 204/412 |
| 3,879,279 | 4/1975 | Baucke | 204/420 |
| 3,883,408 | 5/1975 | Kim et al. | 204/424 |
| 4,105,524 | 8/1978 | Fujishiro et al. | 204/427 |
| 4,172,247 | 10/1979 | Ikeura | 204/427 |
| 4,247,380 | 1/1981 | McIntyre | 204/1 S |
| 4,339,318 | 7/1982 | Tanaka et al. | 204/424 |
| 4,384,935 | 5/1983 | De Jong | 204/425 |
| 4,428,817 | 1/1984 | Isenberg | 204/427 |
| 4,462,872 | 7/1984 | Nelson | 204/428 |
| 4,657,659 | 4/1987 | Mase et al. | 204/412 |
| 4,659,448 | 4/1987 | Gordon | 204/427 |
| 4,661,211 | 4/1987 | Petty-Weeks | 204/424 |
| 4,708,777 | 11/1987 | Kuraoka | 204/1 S |
| 4,735,666 | 4/1988 | Mase et al. | 204/426 |

Primary Examiner—T. Tung
Attorney, Agent, or Firm—Frishauf, Holtz, Goodman & Woodward

[57] ABSTRACT

A solid-state electrochemical analyzer, for measuring the concentration of atoms or molecules in a first fluid or gas as compared with a second fluid or gas, features an insulating tube formed with at least one longitudinal bore therethrough extending from one end, constituting the fluid inlet end of the tube, to the opposite end of the tube, means for directing the first fluid to flow into the longitudinal bore so that the longitudinal bore serves as a path of flow for the first fluid, means defining an outlet for the first fluid, means for directing the second fluid to flow through a second path with respect to the insulating tube, a solid electrolyte, conductive to the ions of the atoms or molecules to be measured, deposited in the insulating tube to bridge the paths of flow of the two fluids, and an electrode, at each of the interfaces of the solid electrolyte with the respective fluid, for outputting an electrical signal generated in the solid electrolyte, the signal corresponding to the concentration of the atoms or molecules in the fluids.

32 Claims, 5 Drawing Sheets

ELECTROCHEMICAL ANALYZER FOR MEASURING THE CONCENTRATION OF ATOMS OR MOLECULES IN A FLUID AND METHOD OF MAKING SAME

The present invention relates to a solid state electrochemical analyzer for measuring the concentration of atoms or molecules in a fluid, and also to a method of making such analyzer. The invention is particularly applicable to analyzers for measuring the concentration of oxygen in a gas, and is therefore described below with respect to this application, but it will be appreciated that the invention could advantageously be used in other applications as well.

Oxygen analyzers are used in many applications, for example in the measurement of the concentration of oxygen in air or in other gasses. Such analyzers usually include an electrochemical cell having a solid electrolyte conductive to oxygen ions. The cell is heated to provide oxygen ion conductivity through the electrolyte, and a voltage is generated between the electrodes when the opposite sides of the electrolyte are subjected to gasses of unequal concentration. Accordingly, if the oxygen concentration in one of the gasses is known, that of the other can be determined.

The electrochemical analyzers heretofore developed are usually very expensive because of the substantially amount of solid electrolyte required and also because of the substantial labour involved to produce them. In addition, the known analyzers generally do not permit precise determination of the temperature of the solid electrolyte at the time of the measurement, which thereby affects the accuracy of the results. Further, in the known analyzers it is generally difficult to determine the partial pressure of the tested fluid (gas) with respect to the standard or reference, because of fluctuation in the total pressure. Still further, the known analyzers usually permit measurements to be made with respect to only two different fluids (e.g. gasses), whereas at times it is necessary or desirable to simultaneously measure the oxygen (or other atom or molecule) concentration in three or more fluids.

An object of the present invention is to provide an electrochemical analyzer having advantages in one or more of the above respects for measuring the concentration of atoms or molecules in one or more fluids, which analyzer is particularly useful for measuring the concentration of oxygen in a gas. Another object is to provide a method of making such an analyzer.

According to the present invention, there is provided an electrochemical analyzer for measuring the concentration of atoms or molecules in a first fluid as compared to a second fluid, comprising: an insulating tube formed with at least one longitudinal bore therethrough extending from one end, constituting the fluid inlet end of the tube, to the opposite end of the tube; means for directing one of the fluids to flow into the longitudinal bore so that the longitudinal bore constitutes a path of flow for the first fluid; means defining an outlet for said first fluid; means for directing the other of the fluids to flow through a second path with respect to the insulating tube; a solid electrolyte, conductive to the ions of the atoms or molecules to be measured, deposited in the tube to bridge the paths of flow of the two fluids; and an electrode at each of the two interfaces of the solid electrolyte with the respective fluid for generating an electrical signal which corresponds to the concentration of the atoms or molecules in the fluids.

A number of embodiments of the invention are described below for purposes of example.

In some described embodiments, the solid electrolyte is deposited in a transverse bore; in one described example of this embodiment, the transverse bore extends from the opposite end of the longitudinal bore to the outer face of the insulating tube, the other fluid being directed to flow over the outer face of the insulating tube.

In another described embodiment, the insulating tube is formed with a second longitudinal bore therethrough defining the path of flow of the other fluid, the solid electrolyte being deposited in a notch formed in the end face of the insulating tube at the opposite end and bringing the two longitudinal bores.

In a further described embodiment, the insulating tube is formed with a second longitudinal bore therethrough defining the path of flow of the other fluid; the solid electrolyte being deposited in a notch formed transversely through the insulating tube adjacent to the opposite end, bridging the two longitudinal bores, and filling the notch and the respective ends of the two longitudinal bores; the insulating tube being further formed with two transverse bores, one extending from each of the longitudinal bores adjacent to their filled ends to the outer suface of the insulating tube to complete the flow paths of the two fluids.

In a still further described embodiment, the insulating tube is formed with a third longitudinal bore defining a flow path for a third fluid; the notch bridging all three of the longitudinal bores at the opposite end of the insulating tube; the solid electrolyte filling the notch at the respective end of the three longitudinal bores; the insulating tube being further formed with a third transverse bore extending from the third longitudinal bore adjacent to its filled end to the outer surface of the insulating tube to complete the flow path of the third fluid.

Electrochemical analyzers constructed in accordance with the foregoing features maybe produced at relatively low cost and capable of producing relatively accurate measurements. The number of fluids that can be accommodated can be increased by merely increasing the number of bore, as will be described more fully below. In addition, as will also be described more fully below, the electrodes may be applied in a simple manner to the interfaces of the solid electrolyte with the respective fluid. In addition, thermocouples may be included in a convenient manner such that the thermocouple junction is close to the solid electrolyte so as to actually measure the temperature there at.

Further features and advantages of the invention will be apparent from the description below.

The invention is herein described, by way of example only with reference to the accompanying drawings, wherein.

Figure 6:
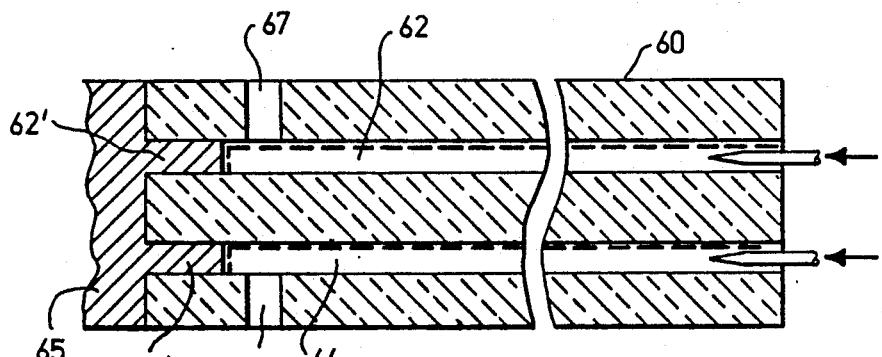
Figure 6A:
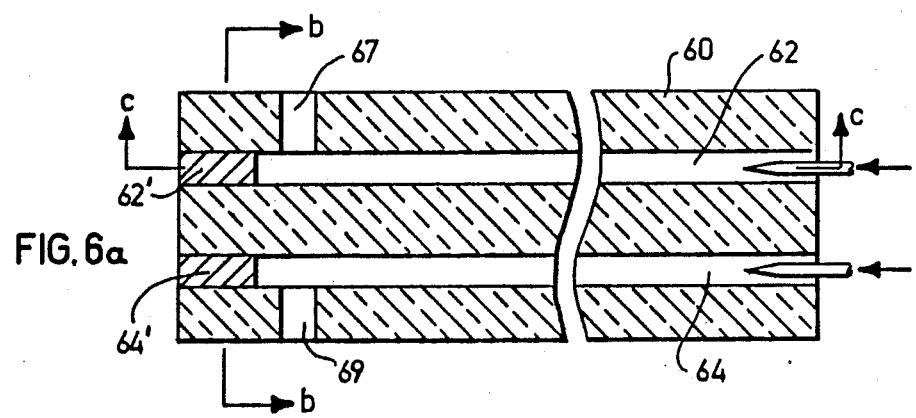
Figure 6B:
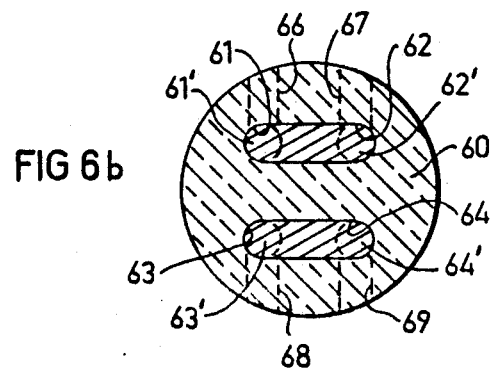
Figure 6C:
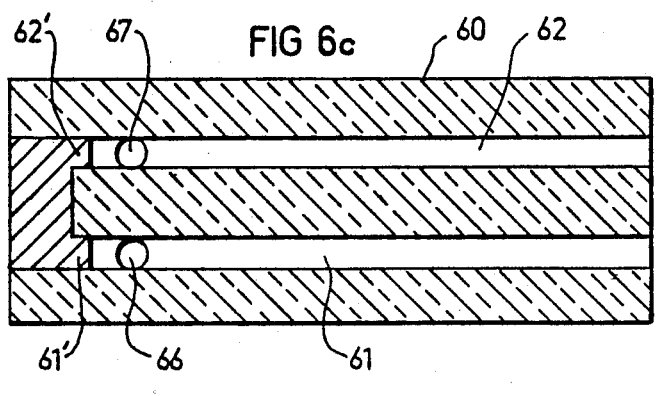

FIG. 6 is a longitudinal sectional view of a still further embodiment of the invention, FIG. 6a being a view similar to that of FIG. 6 but showing a further optional step that may be made in order to convert the analyzer from a single analyzer for simultaneously comparing four gasses, to two distinct analyzers each for comparing two gasses, FIG. 6b being a sectional view along lines b—b of FIG. 6a, and FIG. 6c being a section along lines c—c of FIG. 6a.

Figure 7:
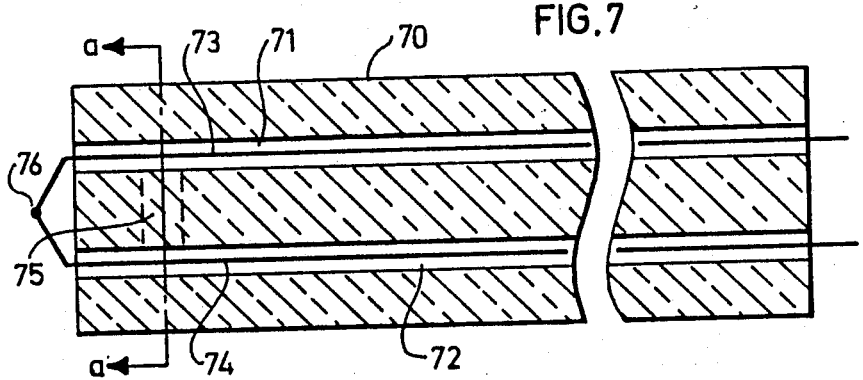
Figure 7A:
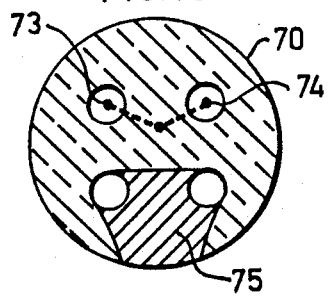
Figure 8A:
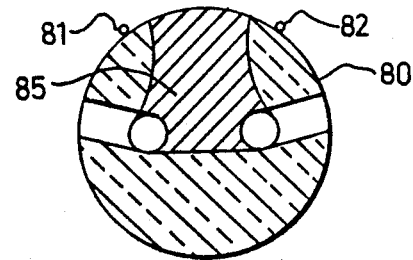
Figure 8:
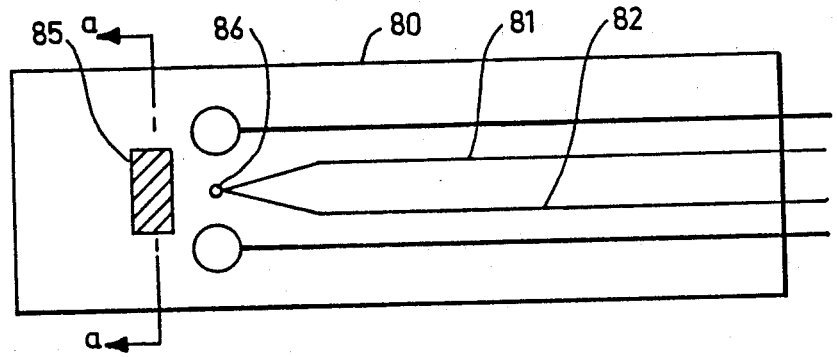
Figure 9:
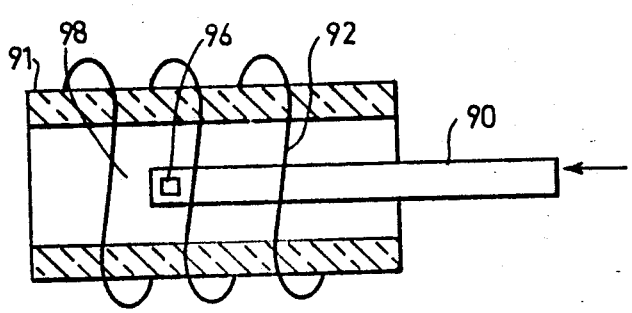

FIG. 7, and its sectional view FIG. 7a, illustrate one arrangement of including a thermocouple in the electrochemical analyzer; and FIG. 8 and its sectional view FIG. 8a illustrate a second arrangement of including the thermocouples in the analyzer; and FIG. 9 is a fragmentary view illustrating one manner of using the analyzer in an electrically-heated tubular oven.

Figure 1:
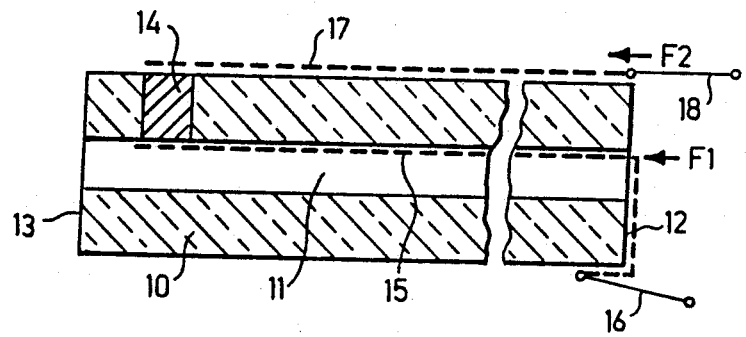
FIG. 1 is a longitudinal sectional view illustrating one form of electrochemical analyzer constructed in accordance with the present invention.

The analyzer illustrated in FIG. 1 comprises an insulating tube, generally designated 10, e.g., of ceramic material, formed with a single longitudinal bore 11 extending therethrough from one end 12 to the opposite end 13. In this embodiment, one gas $F_1$ is directed to flow through longitudinal bore 11 from end 12 of the tube, constituting the fluid inlet end of the tube, to the opposite end 13. A second gas $F_2$ is directed to flow around the outer face of the insulating tube 10.

Insulating tube 10 is provided with a transverse bore filled with a solid electrolyte 14 which bridges the paths of flow of the fluid $F_1$ flowing through longitudinal bore 11 and of the fluid $F_2$ flowing around the outer face of the insulating tube. A first electrode 15 is deposited within longitudinal bore 11 to extend from the solid electrolyte 14 to an electrical lead 16 at the end 12 of the insulating tube; and another electrode 17 is deposited on the outer face of the insulating tube to extend from the solid electrolyte 14 to a second lead 18 at the end 12 of the tube.

It will thus be seen that the two electrodes 15, 17 are connected to the interfaces of the solid electrolyte 14 with the two fluids, namely fluid $F_1$ flowing through bore 11, and fluid $F_2$ flowing along the outer face of the insulating tube. Accordingly, the two electrodes 15, 17 will generate an electrical signal which corresponds to the concentration of the atoms or molecules in the first fluid $F_1$ to be measured, as compared to that in the second fluid $F_2$, or vice versa.

As one example, the two fluids $F_1$, $F_2$ could be gasses containing oxygen; one of the gasses may be a reference whose oxygen concentration is known, the other being one under test to determine the oxygen concentration therein. In this example, the solid electrolyte 14 would be one conductive to the ions of oxygen when heated, so that the electrical signal generated at the output leads 16, 18 would correspond to the oxygen concentration of the tested gas with respect to the reference.

The solid electrolyte 14 may be deposited by plugging the respective end of the longitudinal bore 11, then dipping that end into a bath containing the solid electrolyte 14 to fill the transverse bore, and then removing the plug from the end of the longitudinal bore by drilling. Alternatively, the end of the tube may be dipped into the solid electrolyte without plugging, and then the excess solid electrolyte on the outside, and that filling the end of the longitudinal bore may be removed by a high-speed diamond drill. The electrodes 15, 17 may also be deposited in any suitable manner, for example by applying a paste containing conductive material, and then firing the paste to fix the conductive deposits. The external leads 16, 18 may then be applied by soldering, gluing with conductive glue, or by mechanical attachment.

Figure 2:
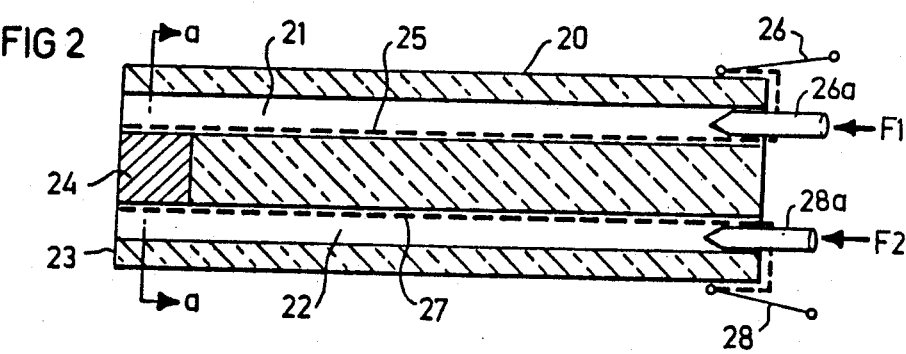
FIG. 2 is a longitudinal view illustrating a second form of electrochemical analyzer constructed in accordance with the present invention, FIG. 2a being a section along line a—a of FIG. 2.
Figure 2A:
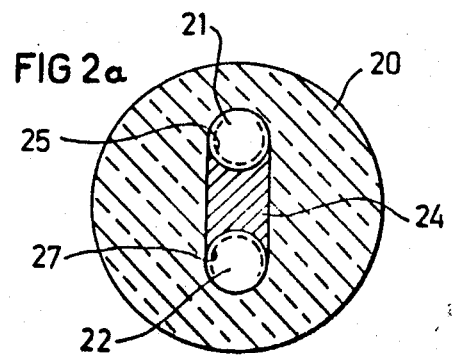

FIG. 2 illustrates a second embodiment of the invention, wherein the insulating tube, generally designated 20, is formed with two longitudinally extending bores 21, 22. Bore 21 serves as the flow path for one fluid $F_1$, and bore 22 serves as the flow path for the other fluid $F_2$. The fluid outlet end 23 of the insulating tube 20 is formed with an end notch, which notch is filled with the solid electrolyte 24 so as to bridge the respective ends of the two longitudinal bores 21, 22. Electrodes 25, 27 are deposited in the two bores 21, 22 to extend from the solid electrolyte 24 to the end of the insulating tube 20 where they are connected to the output terminals 26, 28, respectively. The two electrodes 25, 27 thus connect the interfaces of the solid electrolyte 24 with the respective fluid $F_1$, $F_2$, flowing through the two bores 21, 22, whereby an electrical signal will be generated at the output leads 26, 28 corresponding to the concentration of the atoms or molecules in one fluid with respect to the other.

As shown in FIG. 2, the fluids $F_1$, $F_2$ may be introduced via syringe needles 26a, 28a, whereupon, being useful, they may be brought into electrical contact with the electrode deposits 25, 17 and thus also serve as the output terminals.

Figure 3:
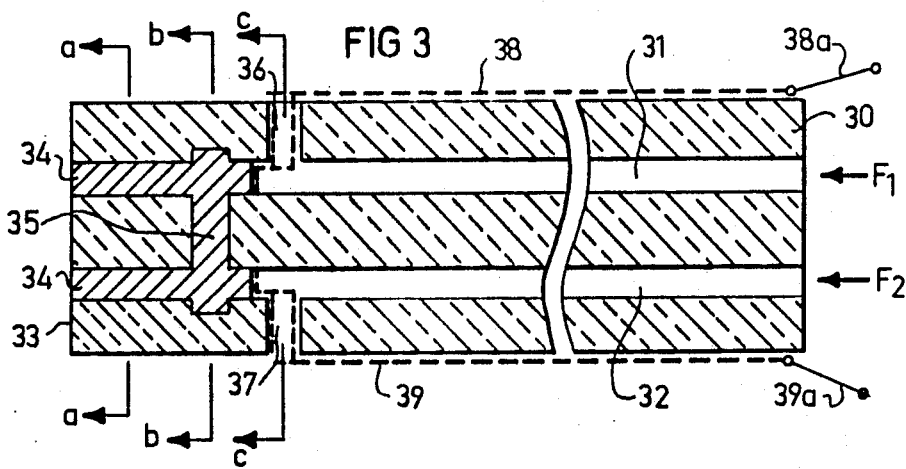
FIG. 3 is a longitudinal sectional view illustrating a further embodiment of the invention, FIGS. 3a, 3b and 3c being sectional views along line a—a, b—b and c—c, respectively, of FIG. 3.

FIG. 3 illustrates a further embodiment of the invention, wherein the insulating tube, generally designated 30, is also formed with two longitudinally extending bores 31, 32, serving as flow paths for the two fluids $F_1$, $F_2$. In this embodiment, however, the ends of the two longitudinal bores 31, 32 at the end 33 of the insulating tube 30 are filled with the solid electrolyte 34, which solid electrolyte also fills a notch 35 bridging the filled ends of the two longitudinal bores 31, 32. Insulating tube 30 is further formed with a transverse bore 36, 37, for each of the longitudinal bores 31, 32, and extending from the respective longitudinal bore, adjacent to the bridging notch 35, to the outer face of the insulating tube. Transverse bores 36, 37 complete the flow paths of the fluids $F_1$, $F_2$ through the longitudinal bores 31, 32.

It will thus be seen that fluid $F_1$ flows through longitudinal bore 31 and out through transverse bore 36, and fluid $F_2$ flows through longitudinal bore 32 and out through transverse bore 37.

The analyzer illustrated in FIG. 3 further includes electrodes 38, 39 extending from the interface of the solid electrolyte 34, 35 with the respective fluid, for generating an electrical signal. This signal appears at the outer leads 38a, 39a, and corresponds to the concentration of the atoms or molecules in one fluid with respect to the other.

Following is one preferred method of making the analyzer of FIGS. 3, 3a–3c.

First, the insulating tube 30 is formed with the two longitudinal bores 31, 32. A notch is then formed adjacent to end 33 of the tube bridging the respective ends of the two longitudinal bores 31, 32 and extending to the outer face of the insulating tube. This may be done, for example, using a drill to form a bore through the side face of the insulating tube to one of the longitudinal bores 31, 32, and then moving the drill laterally in order to enlarge the bore so that it also communicates with the other longitudinal bore.

End 33 of the insulating tube is then dipped into a solid electrolyte in fluid form, such as a heated liquid bath or a fluidized powder bed, to a depth slightly past the notch bridging the ends of the two longitudinal bores 31, 32. The solid electrolyte completely fills the notch and also the respective ends of the two longitudinal bores, as shown at 35 in FIGS. 3 and 3b.

After the solid electrolyte has solidified, the two further transverse bores 36, 37 are formed from the other face of the solid tube to the two longitudinal bores 31, 32, just inwardly of the deposit of solid electrolyte 35. As described above, these transverse bores 36, 37 serve as outlets for the fluids $F_1$, $F_2$ inputted from the opposite ends of the longitudinal bores 31, 32. The electrodes 38, 39 may then be formed in bores 31, 32, in the manner described above, to extend from the interfaces of the solid electrolyte 35 with respect to the two fluids $F_1$, $F_2$ conducted through the two longitudinal bores 31, 32 and outputted through their respective longitudinal bores 31, 32. Preferably, however, and as shown in FIG. 3, the electrodes 38, 39 extend through their transverse bores 36, 37, and then along the outer face of the insulating tube 30 to their respective output leads 38a, 39a.

Figures 3A, 3B, 3C:
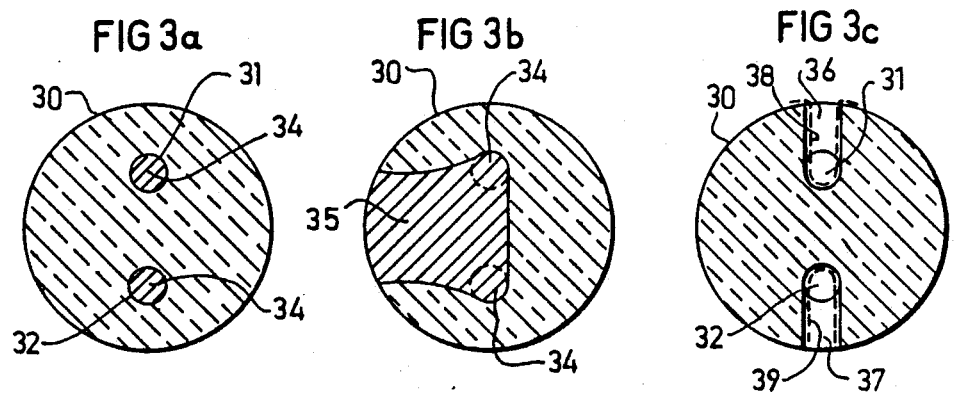
Figure 4:
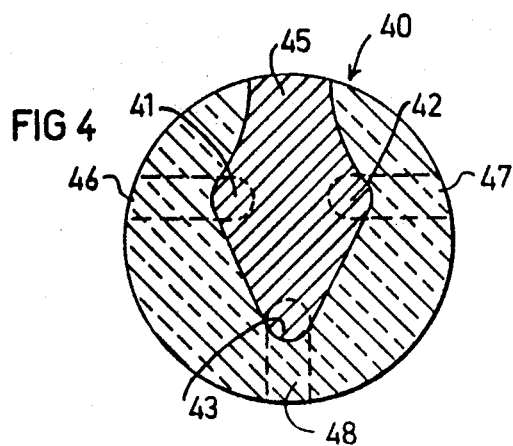
FIG. 4 is a transverse sectional view illustrating a further embodiment of the invention.

FIG. 4 is a view similar to that of FIG. 3b but illustrates a modification in the construction of the analyzer in order to adapt it for accommodating three fluids, rather than two fluids, to permit a comparison to be made as to the relative concentration of a particular atom or molecule, e.g. oxygen, in the three fluids, e.g. gasses. In the modification illustrated in FIG. 4, the insulating tube 40 is formed with three longitudinal bores 41, 42, 43, all three of which are connected by the notch formed through the side of the insulating tube at the end thereof corresponding to end 33 in FIG. 3. This notch, as well as the respective ends of the three longitudinal bores, is filled with the solid electrolyte 45. After the solid electrolyte has been so deposited, three transverse bores 46, 47, 48, corresponding to transverse bores 36, 37 in FIG. 3, are formed to connect with their respective longitudinal bores 41, 42, 43 adjacent to the deposit of the solid electrolyte 45, to thereby complete the flow paths of the fluids through the three longitudinal bores 41, 42, 43.

Figure 5:
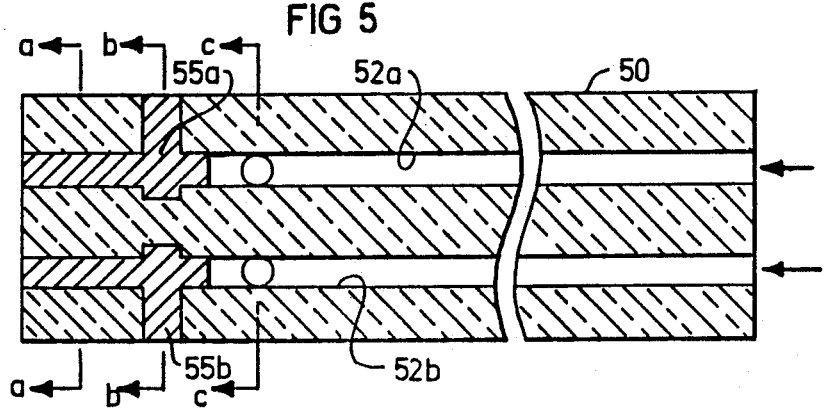
FIG. 5 is a longitudinal sectional view illustrating a still further embodiment of the invention, FIGS. 5a, 5b and 5c being transverse sectional views along line a—a, b—b, and c—c, respectively, of FIG. 5.

FIG. 5 illustrates a further embodiment of the invention wherein a single insulating tube, therein designated 50, is formed as two analyzers, each corresponding to the analyzer illustrated in FIGS. 3–3c.

Thus, in the embodiment illustrated in FIG. 5, insulating tube 50 is formed with four longitudinal bores comprising a first pair 51a, 52a and a second pair 51b, 52b. The bores of pair 51a, 52a are joined at one end with a notch filled with solid electrolyte material 55a, which material also fills the respective ends of the two bores in the same manner as the solid electrolyte materials 35 in FIG. 3. A similar notch is formed bridging the pair of longitudinal bores 51b, 52b and is filled with solid electrolyte material as shown at 55b. In addition, transverse bores 56a, 57a and 56b, 57b, are formed from the outer surface of the insulating tube to the longitudinal bores 51a, 52a and 51b, 52b, to thereby complete the flow paths of the fluid flowing through them.

It will thus be seen that two fluids may be directed to flow through bores 51a, 52a, and out through their transverse bores 56a, 57a, whereupon the solid electrolyte 55a will generate a voltage corresponding to the concentration of the selected atom or molecule in the two fluids; and two further fluids may be directed to flow through longitudinal bores 51b, 52b and out through their respective transverse bores 56b, 57b, whereupon the solid dielectric 55b will generate a voltage corresponding to the concentration of the selected atom or molecule in those two fluids. It will be appreciated that electrodes (not shown in FIG. 5 for the sake of simplicity) are provided at each of the interfaces of the solid electrolyte with the respective fluid for generating the above electrical signals. The electrodes could be applied in the same manner as described above, particularly with respect to FIG. 3. The fluid inlets are also not shown for the sake of simplicity and may be as described above.

Figures 5A, 5B, 5C:
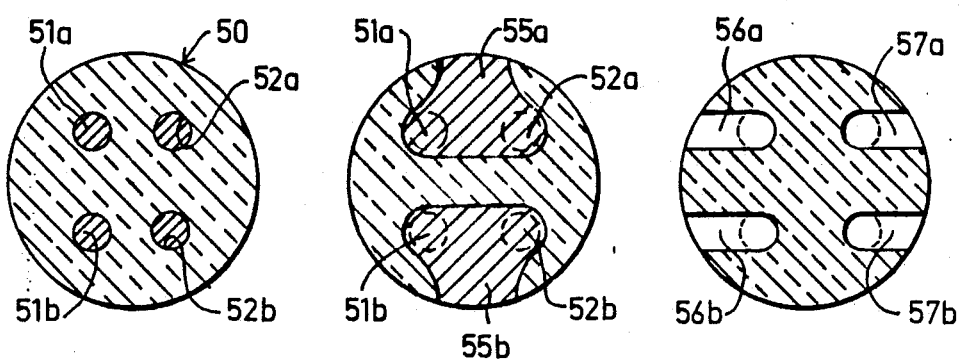

FIGS. 6–6c illustrate another arrangement which may be used for constructing an electrochemical analyzer adapted to accommodate and compare four fluids at one time, or for constructing two distinct analyzers each adapted to accommodate and compare two fluids similar to the arrangement in FIGS. 5–5c.

Thus, the analyzer illustrated in FIGS. 6–6c includes an insulating tube 60 also formed with four longitudinal bores 61–64 extending completely through the tube. One end of the tube, corresponding to end 13 in FIG. 1, is dipped into a bath of solid electrolyte to fill the respective ends of the four bores 61–64, as shown at 61'–64', and also to provide an excess of the solid electrolyte at the ends of the longitudinal bores 61–64. Transverse bores 66–69 are then formed from the outer surface of the insulating tube 60 to the longitudinal bores 61–64 adjacent to the ends of these bores filled with the solid electrolyte. Transverse bores 66–69 thus complete the flow paths of the fluid flowing through the longitudinal bores 61–64.

It will be seen that in the arrangement illustrated in FIG. 6, the excess solid electrolyte 65 bridges the filled ends of the longitudinal bores, and therefore the analyzer can accommodate four fluids simultaneously to measure the selected atom or molecule concentration in the respective fluids. However, it will also be seen that, as shown in FIG. 6c, by adding the end notches as in FIG. 2, and by removing the excess portion of solid electrolyte 65 deposited on the end face of the insulating tube 60, the insulating tube may be converted into two electrochemical analyzers each adapted to accommodate two fluids for measuring the concentration of atoms or molecules therein, somewhat similar to the arrangement described with respect to FIGS. 5–5c.

The analyzers in FIGS. 6–6c would also include the electrodes (not shown) as described above at each of the interfaces of the solid electrolyte with the respective fluid, for generating the electrical signal which corresponds to the concentration of the selected atom or molecule in the respective fluid.

In all of the above-described embodiments, it is desirable to incorporate a thermocouple in the electrochemical analyzer. One way of doing this as shown in FIGS. 7 and 7a, is by merely providing the respective insulating tube 70 with two further longitudinal bores 71, 72, for receiving the thermocouple wires 73, 74, the wires being welded together at the end of the insulating tube adjacent to the solid electrolyte 75 so as to provide the junction 76 producing a measurement of the temperature at the solid electrolyte. Another way, as shown in FIGS. 8 and 8a, is to provide the thermocouple leads (e.g., conductive deposits) 81, 82 on the outer face of the insulating tube 80, and the junction 86 adjacent to the solid electrolyte 85 to define an external thermocouple mounted adjacent to the solid electrolyte.

FIG. 9 illustrates one manner of using the analyzer described above. Thus, the analyzer, generally designated 90, is introduced into a tubular oven 91 having a heating core 92 for heating the analyzer during the time the measurements are taken. The fluid is introduced into the analyzer at its cold end 94, and the solid electrolyte 96 is located in the hot zone 98.

The above-described embodiments of the invention may use many known types of solid electrolytes. For example, in order to sense oxygen concentration in a gas, there may be used inorganic compounds such as zirconium oxide, thorium oxide, cerium oxide or bismuth oxide, all doped with other oxides. The invention may also be used for measuring the concentration of atoms or molecules other than oxygen. For example, the solid electrolyte could be lead fluoride, which conducts negative fluoride ions, and therefore could be used for measurement of fluorine concentrations. In addition, the fluids could be liquids instead of gasses. The conductor deposits for producing the electrodes and for one of the thermocouple leads may be platinum paste, in which case the other thermocouple lead could be platinum paste which includes e.g., 10% rhodium.

It will thus be seen that the electrochemical analyzers described above may be manufactured relatively inexpensively since the procedures are quite simple and the amount of solid electrolyte material used is relatively small. Further, the total pressure of the fluid at the interface with the solid electrolyte is fixed close to the value of the external pressure, which latter pressure can be measured accurately by standard procedures. In addition, the temperature at the solid electrolyte can also be measured quite accurately.

While the invention has been described with respect to several preferred embodiments, it will be appreciated that many other variations, modifications and applications of the invention may be made.

What is claimed is:

1. A solid state electrochemical analyzer for measuring the concentration of atoms or molecules in a first fluid as compared to a second fluid and to a third fluid, comprising:
   an insulating tube (30, 40) formed with at least three longitudinal bores (31, 32; 41, 42, 43) therethrough extending from one end, constituting the fluid inlet end (12) of the tube, to the opposite end (13, 23, 33) of the tube;
   means for directing said first, second and third fluids to flow into respective first, second and third ones (41, 42, 43) of said longitudinal bores so that said longitudinal bores constitute respective paths of flow for said first, second and third fluids;
   means (36, 46; 37, 47; 48) defining outlets for said first, second and third fluids;
   a single solid electrolyte (35, 45), conductive to the ions of said atoms or molecules to be measured, deposited in a cavity formed in said tube (30, 40), contacting sidewalls of said cavity, and bridging said paths of flow of said first, second, and third fluids;
   and a respective electrode (15, 17; 25, 27; 38, 39) at each of the interfaces of the solid electrolyte (35, 45, 55) with the respective fluid for outputting an electrical signal, generated in said solid electrolyte, corresponding to the concentration of the atoms or molecules in the fluids.

2. The analyzer according to claim 1, wherein said solid electrolyte is deposited in at least one transverse bore formed in said insulating tube.

3. The analyzer according to claim 2, wherein each transverse bore extends from a longitudinal position adjacent said opposite end (13) of the longitudinal bore to the outer surface of the insulating tube.

4. The analyzer according to claim 1, wherein
   said solid electrolyte is deposited in a notch formed in an end face of the insulating tube at said opposite end (13) and bridges said longitudinal bores.

5. The analyzer according to claim 1, wherein
   said solid electrolyte is deposited in a notch formed transversely through said insulating tube adjacent to said opposite end, said solid electrolyte bridging said longitudinal bores, and filling said notch and the respective ends of the longitudinal bores; and
   said insulating tube is further formed with one transverse bore from each of the longitudinal bores adjacent to their ends containing said solid electrolyte to the outer surface of the insulating tube to complete the flow paths of the respective fluids.

6. The analyzer according to claim 1, wherein said solid electrolyte consists essentially of inorganic material.

7. The analyzer according to claim 6, wherein said inorganic solid electrolyte consists essentially of metal oxide and said ions are oxygen ions.

8. The analyzer according to claim 6, wherein said inorganic solid electrolyte consists essentially of metal fluoride and said ions are fluoride ions.

9. The analyzer according to claim 1, wherein the insulating tube is of a ceramic material.

10. The analyzer according to claim 1, wherein said solid electrolyte is of a material conductive to oxygen ions to measure the concentration of oxygen in said first fluid.

11. The analyzer according to claim 1, further including
    two further longitudinal bores, and a thermocouple wire extending through each of said latter bores;
    said thermocouple wires meeting at a thermocouple junction adjacent to said solid electrolyte deposit.

12. The analyzer according to claim 1, wherein
    said insulating tube carries, on its outer face, a pair of conductive deposits defining thermocouple leads coming to a junction adjacent to said solid electrolyte deposit and are connected to electrical terminals at said fluid inlet end of the insulating tube.

13. The analyzer according to claim 1, wherein
    said electrodes are in the form of conductive deposits extending through said longitudinal bores into contact with the respective solid electrolyte deposit, and are connected to electrical terminals at said fluid inlet end of the insulating tube.

14. The analyzer according to claim 13, wherein said electrode deposits also extend partly along the outer surface of the insulating tube.

15. The analyzer according to claim 1, further including tubes serving as the fluid inlets into their respective bores.

16. The analyzer according to claim 15, wherein said tubes are of a conductive materials and establish electrical contact with the electrodes which extend through the bores.

17. The analyzer according to claim 1, further including
an outer tubular oven round said insulating tube, and
an electrical heater for heating the end of said insulating tube having said deposit of solid electrolyte.

18. The method according to claim 1, wherein said insulating tube is formed with four longitudinal bores, each filled at one end with the solid electrolyte, and each connected to the outer face of the insulating tube by a transverse bore to complete the fluid flow path of the respective longitudinal bore.

19. A solid state electrochemical analyzer for measuring the concentration of oxygen in a first fluid as compared to a second fluid and in a third fluid as compared to a fourth fluid, comprising (FIGS. 5b, 6b)
a single insulating tube (50, 60) formed with four longitudinal bores (51a–52b; 61–64) therethrough extending from one end, constituting the fluid inlet end (12) of the tube, to the opposite end (13) of the tube, and two notches remote from said inlet end (12), each notch interconnecting two of said bores,
means for directing said first through fourth fluids to flow into respective first through fourth ones of said longitudinal bores (51a–52b; 61–64 so that said longitudinal bores constitute respective paths of flow for said first through fourth fluids;
means (56a, 57b; 66–69) defining respective outlets for said fluids;
solid electrolyte (55, 65), conductive to oxygen ions, deposited in and contacting sidewalls of said interconnecting notches and bridging said paths of flow of said fluids, each such longitudinal bore (51–52; 61–64) being connected to the outer surface of the insulating tube (50, 60) by a transverse bore (56a, 56b, 57a, 57b; 66, 67, 68, 69) to complete the fluid flow path of the respective longitudinal bore;
and a respective electrode (15, 17; 25, 27; 38, 39) at each of the interfaces of the solid electrolyte (55, 65) with the respective fluid, at least one of said electrodes extending along an outer surface of said insulating tube, for outputting an electrical signal, generated in said solid electrolyte (55, 65), corresponding to the relative concentrations of oxygen in the fluids.

20. A method of making a solid state electrochemical analyzer for measuring the concentration of atoms or molecules in a first fluid as compared to a second fluid and to a third fluid, comprising the steps of:
providing an insulating tube having at least two longitudinal bores extending from one end, constituting the fluid inlet end of the tube, to a respective fluid outlet at an opposite, fluid outlet end of the tube, to define a path of flow for said first and second fluids, said tube including a path of flow for said third fluid;
depositing a single solid electrolyte, conductive to the ions of said atoms or molecules to be measured, in said tube immediately adjacent each path of flow to bridge said paths of flow of said first, second, and third fluids;
and applying an electrode at each of the interfaces of the single solid electrolyte with the respective fluid, at least one of said electrodes extending along an outer surface of said insulating tube, for outputting a respective electrical signal, generated in said solid electrolyte, corresponding to the relative concentrations of the atoms or molecules in the fluids.

21. The method according to claim 20, including forming a transverse bore adjacent to said opposite end of the insulating tube, said solid electrolyte being deposited in said transverse bore.

22. The method according to claim 20, wherein said insulating tube is provided with a third longitudinal bore therethrough defining said path of flow of said third fluid, said solid electrolyte being deposited in a notch formed in the end face of the insulating tube at said opposite end and bridging said three longitudinal bores.

23. The method according to claim 20, wherein said insulating tube is formed with a third longitudinal bore therethrough defining said path of flow of said third fluid; said solid electrolyte being deposited in a notch formed transversely through said insulating tube adjacent to said opposite end, bridging said three longitudinal bores, and filling said notch and the respective ends of the three longitudinal bores; said insulating tube being further formed with three transverse bores, one from each of the longitudinal bores adjacent to their filled ends to the outer surface of the insulating tube to complete the flow paths of the three fluids.

24. The method according to claim 20, wherein said electrodes are applied in the form of conductive deposits extending through said longitudinal bores into contact with the respective solid electrolyte deposit, and are connected to electrical terminals at said fluid end of the insulating tube.

25. The method according to claim 24, wherein said electrode deposits are also applied to extend partly along the outer surface of the insulating tube.

26. The method according to claim 20, further comprising the step of providing a thermocouple in the form of two conductors (71, 72; 81, 82), each passing through a respective one of said bores.

27. The method according to claim 20, further comprising the step of providing a thermocouple whose leads are in the form of conducting deposits applied to the outer surface of the insulating tube.

28. A solid state electrochemical analyzer for measuring the concentration of oxygen in a first fluid as compared to a second fluid, comprising:
a single insulating tube (30, 40, 50, 60, 70) formed with at least two longitudinal bores (31–32; 41–43; 51a–52b; 61–62) therethrough extending from one end, constituting the fluid inlet end (12) of the tube, to the opposite end (13, 23, 33) of the tube, and a cavity intermediate said tube ends and connecting with said longitudinal bores;
means for directing said first and second fluids to flow into respective first and second ones (31, 32; 41, 42) of said longitudinal bores so that said longitudinal bores constitute respective paths of flow for said first and second fluids;
means (36, 46; 37, 47) defining outlets for said first and second fluids;
a single solid electrolyte (35, 45, 55), conductive to oxygen ions, deposited in said cavity formed in said tube (30, 40, 50, 60, 70), contacting sidewalls of said cavity and completely filling a transverse dimension thereof, to bridge said paths of flow of said first and second fluids, said cavity being shaped to detain said electrolyte therein against movement with respect to said insulating tube;

and a respective electrode (15, 17; 25, 27; 38, 39) at each of the interfaces of the solid electrolyte (35, 45, 55) with the respective fluid, at least one (17) of said electrodes extending along an outer surface of said insulating tube, for outputting an electrical signal, generated in said solid electrolyte, corresponding to the relative concentrations of oxygen in the fluids.

29. A solid state electrochemical analyzer for measuring the concentration of atoms or molecules in a first fluid as compared to a second fluid and to a third fluid, comprising:

an insulating tube (60) formed with at least three longitudinal bores (61, 62, 63) therethrough extending from one end, constituting the fluid inlet end (12) of the tube, to the opposite end (13) of the tube;

means for directing said first, second and third fluids to flow into respective first, second and third ones (61, 62, 63) of said longitudinal bores so that said longitudinal bores constitute respective paths of flow for said first, second and third fluids;

means (66, 67, 68), remote from said fluid inlet end (12), defining outlets for said first, second and third fluids;

a single solid electrolyte (65), conductive to the ions of said atoms or molecules to be measured, deposited on said opposite end (13) of said tube to bridge said paths of flow of said first, second, and third fluids;

and a respective electrode (15, 17; 25, 27; 38, 39) at each of the interfaces of the solid electrolyte (65) with the respective fluid for outputting an electrical signal, generated in said solid electrolyte, corresponding to the concentration of the atoms or molecules in the fluids.

30. A method of making a solid state electrochemical analyzer for measuring the concentration of atoms or molecules in a first fluid as compared to a second fluid and to a third fluid, comprising:

providing an insulating tube (60) formed with at least three longitudinal bores (61, 62, 63) therethrough extending from one end, constituting the fluid inlet end (12) of the tube, to the opposite end (13) of the tube, said longitudinal bores defining respective paths of flow for said first, second and third fluids;

depositing a single solid electrolyte (65), conductive to the ions of said atoms or molecules to be measured, on said opposite end (13) of said tube, to bridge said paths of flow of said first, second, and third fluids;

and applying a respective electrode (15, 17; 25, 27; 38, 39) at each of the interfaces of the solid electrolyte (65) with the respective fluid for outputting an electrical signal, generated in said solid electrolyte, corresponding to the concentration of the atoms or molecules in the fluids.

31. A method of making a solid state electrochemical analyzer for measuring the concentration of oxygen in a first fluid as compared to a single fluid, comprising:

providing a single insulating tube (30, 40, 50, 60, 70) formed with at least two longitudinal bores (31–32; 41–43; 51a–52b; 61–62) therethrough extending from one end, constituting the fluid inlet end (12) of the tube, to the opposite end (13, 23, 33) of the tube, and a cavity intermediate said tube ends and connecting with said longitudinal bores, said longitudinal bores defining respective paths of flow for said first and second fluids;

depositing a single solid electrolyte (35, 45, 55), conductive to oxygen ions, in said cavity formed in said tube (30, 40, 50, 60, 70), contacting sidewalls of said cavity and completely filling a transverse dimension thereof, to bridge said paths of flow of said first and second fluids, said cavity being shaped to detain said electrolyte therein against movement with respect to said insulating tube;

and applying a respective electrode (15, 17; 25, 27; 38,39) at each of the interfaces of the solid electrolyte (35, 45, 55) with the respective fluid, at least one (17) of said electrodes extending along an outer surface of said insulating tube, for outputting an electrical signal, generated in said solid electrolyte, corresponding to the relative concentrations of oxygen in the fluids.

32. A method of making a solid state electrochemical analyzer for measuring the concentration of atoms or molecules in a first fluid as compared to a second fluid and in a third fluid as compared to a fourth fluid, comprising (FIGS. 5b, 6b)

providing a single insulating tube (50, 60) formed with four longitudinal bores (51a–52b; 61–64) therethrough extending from one end, constituting the fluid inlet end (12) of the tube, to the opposite end (13) of the tube, thereby defining a respective path of flow for each of said fluids, and two notches remote from said inlet end (12), each notch interconnecting two of said bores, depositing solid electrolyte, conductive to the ions of said atoms or molecules to be measured, in each of said notches of said tube, contacting sidewalls of said notches, and immediately adjacent each path of flow, to bridge said paths of flow of said fluids;

and applying an electrode at each of the interfaces of the solid electrolyte with the respective fluid, at least one of said electrodes extending along an outer surface of said insulating tube, for outputting a respective electrical signal, generated in said solid electrolyte, corresponding to the relative concentrations of the atoms or molecules in the fluids.

* * * * *